United States Patent [19]

Akutsu et al.

[11] Patent Number: 4,707,507
[45] Date of Patent: Nov. 17, 1987

[54] 2,2,6,6-TETRAMETHYL QUATERNARY AMMONIUM HALIDES AND SYNTHETIC RESIN AND STABILIZER COMPOSITIONS

[75] Inventors: Mitsuo Akutsu, Tokyo; Mitsuharu Kanai, Saitama, both of Japan

[73] Assignee: Adeka Argus Chemical Co., Ltd., Urawa, Japan

[21] Appl. No.: 904,130

[22] Filed: Sep. 4, 1986

[30] Foreign Application Priority Data

Sep. 4, 1985 [JP] Japan ................. 60-195564

[51] Int. Cl.$^4$ .............................. C08K 5/34
[52] U.S. Cl. ..................... 524/99; 524/103; 546/186; 546/244; 252/401
[58] Field of Search .............. 524/99, 103; 546/186, 546/244; 252/401

[56] References Cited

U.S. PATENT DOCUMENTS

| | | | |
|---|---|---|---|
| 2,758,114 | 8/1956 | Miescher et al. | 546/186 |
| 2,922,786 | 1/1960 | De Witt | 546/186 |
| 3,055,902 | 9/1962 | Walker | 546/186 |
| 3,499,903 | 3/1970 | Minisci et al. | 546/186 |
| 3,904,581 | 9/1975 | Murayama et al. | 524/99 |

FOREIGN PATENT DOCUMENTS

| | | | |
|---|---|---|---|
| 0164143 | 10/1982 | Japan | 524/99 |
| 1249081 | 12/1983 | U.S.S.R. | 524/99 |

*Primary Examiner*—John Kight
*Assistant Examiner*—Kriellion Morgan

[57] ABSTRACT

Water-soluble or dispersible 2,2,6,6-tetramethylquaternary ammonium halides are provided, effective as stabilizers to increase the resistance to deterioration when exposed to light of synthetic resins, and having the formula:

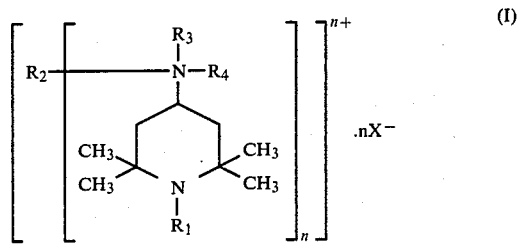

wherein:
$R_1$, $R_3$ and $R_4$ are alkyl having from one to about twelve carbon atoms;
n is 1 or 2;
when n is 1, $R_2$ is alkyl having from one to about twelve carbon atoms; and
when n is 2, $R_2$ is alkylene having from one to about twelve carbon atoms; and
X is halogen as well as stabilizer compositions and synthetic resin compositions containing the same.

23 Claims, No Drawings

2,2,6,6-TETRAMETHYL QUATERNARY AMMONIUM HALIDES AND SYNTHETIC RESIN AND STABILIZER COMPOSITIONS

Many synthetic resins, such as polyethylene, polypropylene, polyvinyl chloride and ethylene-vinyl acetate copolymer, have a low resistance to deterioration when exposed to ultraviolet light, and many types of compounds have been proposed as light stabilizers to inhibit such deterioration.

One of the most widely-used types of light stabilizers is the 2,2,6,6-tetramethyl-piperidyl compounds. However, these compounds are not water-soluble, and cannot therefore be used when water solubility or dispersibility is important, such as where compatibility with aqueous solution or dispersions containing hydrophilic polymers is required.

In accordance with the present invention, water-soluble or dispersible 2,2,6,6-tetramethyl quaternary ammonium halides are provided, having the formula:

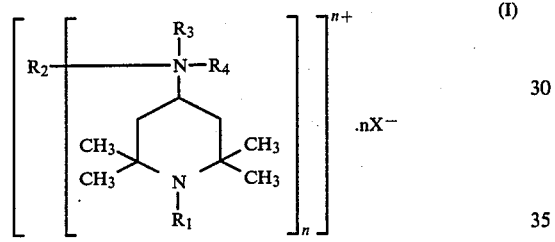

wherein:
$R_1$, $R_3$ and $R_4$ are alkyl having from one to about twelve carbon atoms;
n is 1 or 2;
when n is 1, $R_2$ is alkyl having from one to about twelve carbon atoms; and
when n is 2, $R_2$ is alkylene having from one to about twelve carbon atoms; and
X is halogen.

Exemplary $R_1$, $R_2$, $R_3$ and $R_4$ alkyl include methyl, ethyl, propyl, iso-propyl, butyl, iso-butyl, tert-butyl, amyl, iso-amyl, tert-amyl, hexyl, iso-hexyl, heptyl, octyl, iso-octyl, 2-ethylhexyl, nonyl, iso-nonyl, tert-nonyl, decyl, undecyl and dodecyl.

Exemplary $R_2$ alkylene (n is 2) include methylene, ethylene, propylene, butylene, pentylene, neopentylene, hexylene, heptylene, octylene, nonylene, decylene, undecylene and dodecylene, linked to the nitrogen in any of the following configurations: 1,2; 1,3; 1,4; 1,5; 1,6; 1,7; 1,8; 1,9; 1,10; 1,11; 1,12; 2,4; 2,5; 2,6; 3,4; 3,5; 3,6; 3,7; 3,8; 4,10 and 4,12. As will be apparent from this exemplification, the alkylene group can be straight or branched chain, in any configuration, with any number of carbon atoms in the chain directly linking the two nitrogens of the quaternary ammonium groups.

Typical compounds falling within Formula I include:

1. 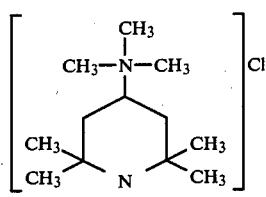

2. 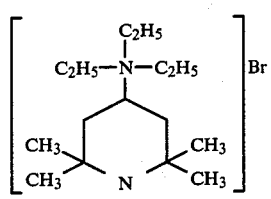

3. 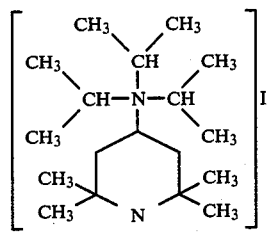

4. 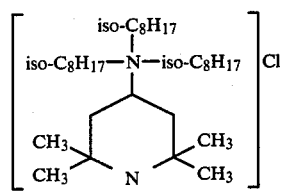

5. 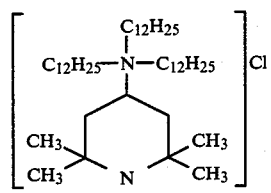

6. 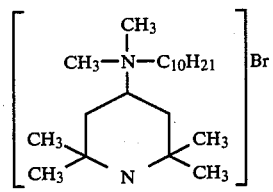

7. 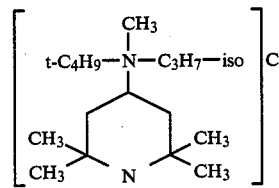

-continued

8. 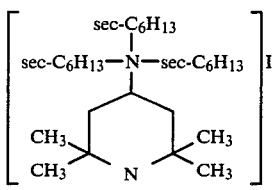

9. 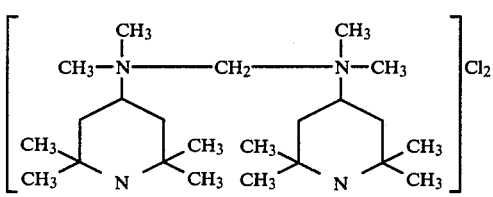

10. 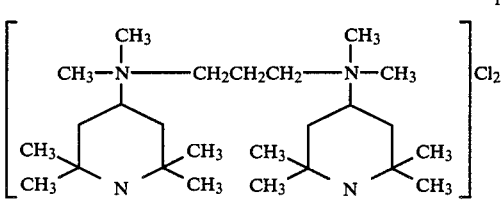

11. 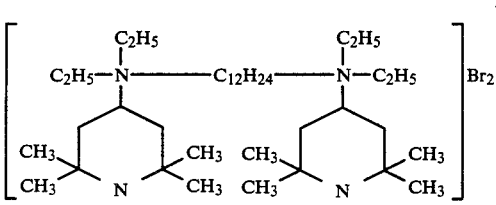

12. 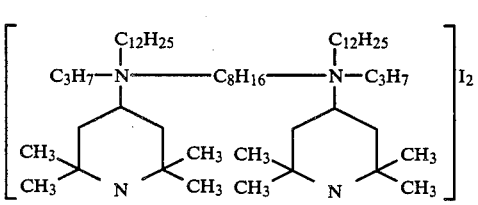

13. 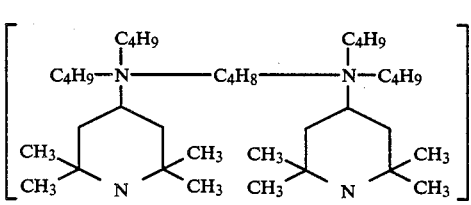

14. 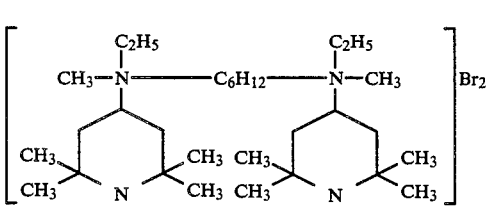

The 2,2,6,6-tetramethyl-quaternary ammonium halides of the invention are readily prepared by reaction with an alkyl halide $R_4X$, where $R_4$ and $X$ are as above, with a piperidyl amine having the formula:

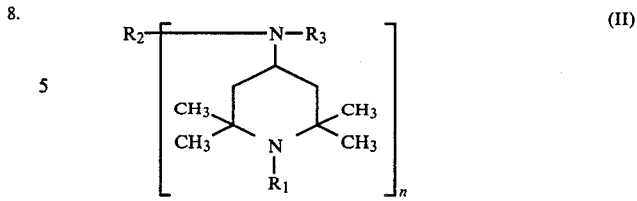

The following preparations are exemplary.

EXAMPLE I

Preparation of N,N-Dimethyl-N-butyl-N-(1,2,2,6,6-pentamethyl-4-piperidyl)ammonium bromide N-Methyl-N-butyl-N-(1,2,2,6,6-pentamethyl-4-piperidyl)amine 18 g and 80 ml ethanol were placed in an autoclave, and cooled to 0° C., whereupon 23 g of methyl bromide was added. The mixture was stirred for one hour at room temperature, and then heated to 60° C. and stirred for 3 hours. Ethanol and unreacted methyl bromide were distilled off. The resulting solid was recrystallized from dioxane, and 19.6 g of pale yellow crystals melting at 159°–160° C. was obtained.

The compound was soluble in water in amounts up to about 15 g per 100 g of water at room temperature.

Analytical results of the product are:

NMR (δ value) 3.9–3.4 ppm: 3H, multiple, 3.29 ppm: 6H, s, 2.23 ppm: 3H, s.

| | Elemental analysis: | | |
|---|---|---|---|
| | C % | H % | N % |
| Calcd. | 57.30 | 10.52 | 8.35 |
| Found | 56.85 | 10.44 | 8.27 |

EXAMPLE II

Preparation of N,N-Dimethyl-N-butyl-N-(1,2,2,6,6-pentamethyl-4-piperidyl)ammonium iodide N-Methyl-N-butyl-N-(1,2,2,6,6-pentamethyl-4-piperidyl)amine 9.6 g was dissolved in 10 ml of ethanol, and then 6 g of methyl iodide was added dropwise at room temperature. The mixture was stirred for one hour at room temperature, and then heated to reflux and stirred under reflux for an additional hour. The ethanol and unreacted methyl iodide were distilled off. The resulting solid was washed with diethyl ether, and 11.2 g white crystals melting at 184°–186° C. was obtained. The crystals were water soluble.

Analytical results were as follows:

NMR (δ value) 3.9–3.3 ppm: 3H, multiple, 3.27 ppm; 6H, s, 2.22 ppm: 3H, s.

| | Elemental analysis: | | |
|---|---|---|---|
| | C % | H % | N % |
| Calcd. | 50.26 | 9.23 | 7.33 |
| Found | 49.87 | 9.17 | 7.25 |

EXAMPLE III

Preparation of
N,N-Dimethyl-N-octyl-N-(1,2,2,6,6-pentamethyl-4-piperidyl)ammonium iodide N-Methyl-N-octyl-N-(1,2,2,6,6-pentamethyl-4-piperidyl)amine 7.4 g was dissolved in 15 ml of ethanol and 3.8 g methyl iodide added dropwise at room temperature. After stirring for two hours at room temperature the reaction mixture was heated to reflux and then stirred an additional four hours. Ethanol and unreacted methyl iodide were distilled off. The resulting solid was washed with diethylether. 9.5 g pale yellow crystals melting at 153°–154° C. was obtained. The solid was water-soluble.

Analytical results were as follows:

NMR ($\delta$ value) 3.9–3.4 ppm: 3H, multiple, 3.27 ppm: 6H, s, 2.19 ppm: 3H, s.

|  | Elemental analysis: | | |
|---|---|---|---|
|  | C % | H % | N % |
| Calcd. | 54.78 | 9.88 | 6.39 |
| Found | 54.33 | 9.80 | 6.34 |

EXAMPLE IV

Preparation of
N,N,N',N'-Tetramethyl-N,N'-bis(1,2,2,6,6-pentamethyl-4-piperidyl)hexamethylene diammonium diiodide N,N'-Dimethyl-N,N'-bis(1,2,2,6,6-pentamethyl-4-piperidyl)-hexamethylene diamine 6.3 g was dissolved in 15 ml of ethanol and 4.7 g of methyl iodide added dropwise at room temperature. The reaction mixture was stirred for 30 minutes at room temperature, then heated to 75° C., and stirred at 75° C. an additional 30 minutes. The precipitated material was filtered off and washed with ethanol. 10.2 g white crystals was obtained, decomposing at 276° C., and soluble in water.

Analytical results were as follows:

NMR ($\delta$ value) 4.0–3.4 ppm: 3H, multiple, 3.27 ppm: 6H, s, 2.21 ppm: 3H, s.

|  | Elemental analysis: | | |
|---|---|---|---|
|  | C % | H % | N % |
| Calcd. | 49.05 | 8.78 | 7.63 |
| Found | 49.57 | 8.82 | 7.71 |

These compounds are quaternary ammonium salts, and therefore are water-soluble or water-dispersible, forming water solutions or dispersions containing up to 10% by weight of the piperidyl quaternary ammonium halide. They accordingly can be used as light stabilizers in aqueous coating solutions and dispersions containing water-soluble or water-dispersible synthetic polymers, such as latex paints; aqueous systems containing polyvinyl alcohol, partially hydrolyzed polyvinyl acetate, and polyvinyl pyrollidone; water soluble and water dispersible cellulose ethers; surfactants having a synthetic polymer backbone; emulsified waxes; and water-solbuel fats and oils and fatty acid esters.

Quaternary ammonium compounds containing surface-active groups, such as polyoxyalkylene groups and long chain aliphatic groups, can be used as surfactants, and the piperidyl quarternary ammonium compounds of the invention when containing such groups combine effectiveness as a light stabilizer with surface activity, thus rendering them useful in a wide range of aqueous solutions and dispersions containing ingredients such as synthetic resins, hydrocarbon waxes, fatty oils, acids and esters and other ingredients that are subject to deterioration when exposed to ultraviolet light. Groups imparting surfactant activity to the piperidyl quaternary ammonium compounds of the invention include long chain aliphatic groups having from eigh to about twenty-two carbon atoms, and polyoxyalkylene groups having from six to about forty oxyalkylene units of from two to four carbon atoms, such as oxyethylene, oxypropylene and oxybutylene. Examples of such compounds include:

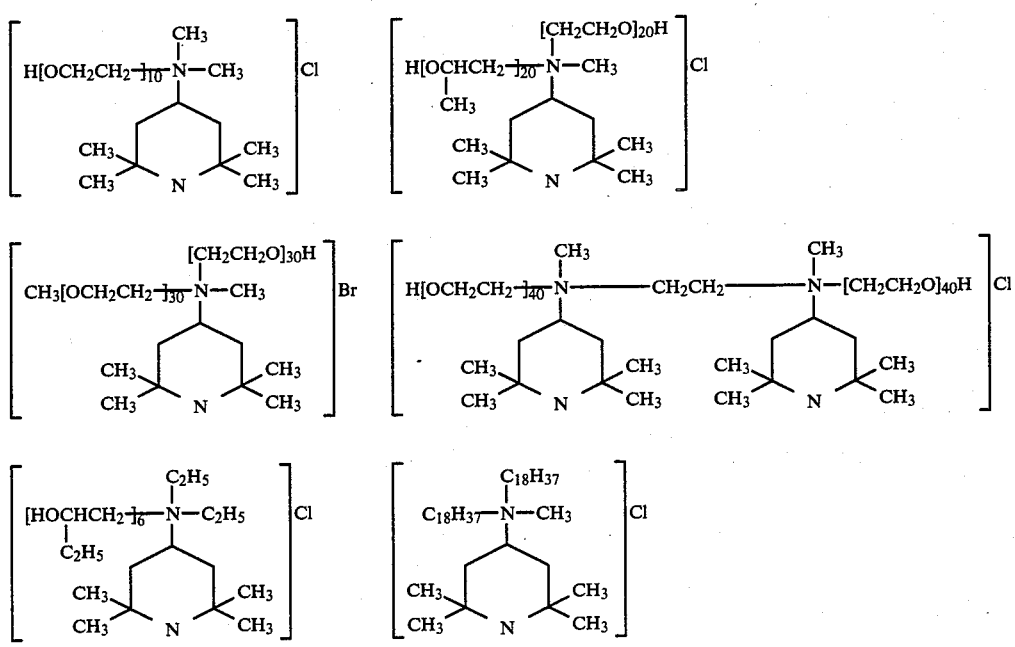

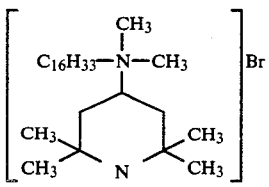 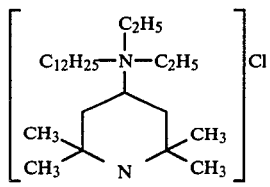

The piperidyl quaternary ammonium compounds of the invention are particularly useful as light stabilizers in photosensitive coatings and coating compositions used for photography, photolithography, and other photosensitive systems. The compounds enhance the resistance to deterioration upon exposure to ultraviolet light of such compositions while not interfering with photosensitivity, and their water-solubility and water-dispersibility renders them more compatible with such compositions and coatings.

The piperidyl quaternary ammonium compounds of the invention are also useful light stabilizers in latex paints, which are aqueous emulsions containing synthetic resins subject to deterioration upon exposure to ultraviolet light. These light stabilizers enhance the stability of the paint emulsion, as well as of the paint coating obtained upon application of such coatings to a surface, and are particularly useful in outdoor type latex paint compositions.

The piperidyl quaternary ammonium compounds also are useful to increase the resistance to deterioration upon exposure to ultraviolet light of water-soluble and water-dispersible dyestuffs and pigments, lessening their tendency to fade and change color. The compounds can be incorporated in the composition for applying the dyestuffs or pigments to the substrate.

Small amounts of the piperidyl quaternary ammonium halides of this invention when combined with synthetic resin improve the light stability of the resin. The amount of the piperidyl quaternary ammonium halides is generally within the range from about 0.001 to about 10 parts by weight, preferably from about 0.01 to about 3 parts by weight, per 100 parts by weight of resin.

Because of their water solubility or dispersibility, the piperidyl quaternary ammonium halides are particularly useful with hydrophilic water soluble or water dispersible synthetic resins and synthetic resin compositions. However, they are also useful with any synthetic resin or resin composition.

Synthetic resins that can have their resistance to deterioration enhanced with piperidyl quaternary ammonium halides according to this invention include polyvinyl alcohol, partially hydrolyzed polyvinyl acetate, α-olefin polymers such as polyethylene, polypropylene, polybutene, poly-3-methylbutene, or mixtures thereof and with copolymers other monomers such as ethylene-vinyl acetate copolymer, ethylene-propylene copolymer; polystyrene; polyvinyl acetate; polyacrylic esters; copolymers from styrene and another monomer (for example, maleic anhydride, butadiene, and acrylonitrile); acrylonitrile-butadiene-styrene copolymer, acrylic acid ester-butadiene-styrene copolymer, methacrylic acid ester butadiene-styrene copolymer, polymethacrylate esters such as polymethacrylate; polyvinyl alcohol; polyvinyl formal; polyvinyl butyral; linear polyesters, polyamides; polycarbonates; polyacetals; polyurethanes; cellulosic resins; phenol-formaldehyde resins; urea-formaldehyde resins; melamine-formaldehyde resins; epoxy resins; unsaturated polyester resins; silicone resins; halogen-containing resins such as polyvinyl chloride, polyvinylidene chloride, polyvinylidene fluoride, and copolymers thereof, and rubbers such as isoprene rubber, butadiene rubber, epichlorohydrin rubber, chloroprene rubber, and blends of any of the above.

The piperidyl quaternary ammonium halides of the invention can be combined with conventional heat stabilizers such as phenolic antioxidants, polyvalent metal salts of organic acids, organic phosphites, thioethers, and other known heat stabilizers, thereby constituting light and heat stabilizer compositions of the invention. The water-soluble and water dispersible stabilizers are preferred for use with aqueous solutions and dispersions of the piperidyl quaternary ammonium halides.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicylidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of biyclic phenols, the rings can be linked by thio or oxyether groups, or by alkylene, alicyclidene or arylidene groups.

The monocyclic phenols which can be employed have the structure:

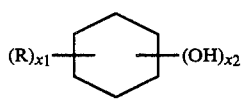

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl

where R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

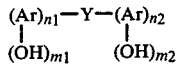

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarboxylic group having condensed or separate phenyl rings; each Ar group contains at least one free phenolic hydroxyl group up to a total of five. The Ar rings can also include additional rings connected by additional linking nuclei of the type Y, for example, Ar-Y-Ar-Y-Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen, halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy

where R' is aryl, alkyl or cycloalkyl, or thiohydrocarbon groups having from one to about thirty carbon atoms, and carboxyl

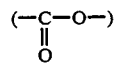

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

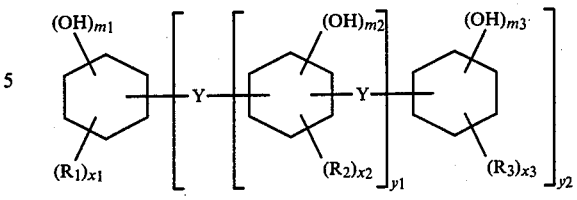

wherein $R_1$, $R_2$ and $R_3$ are inert substituent groups as described in the previous paragraph;

$m_1$ and $m_3$ are integers from one to a maximum of five;

$m_2$ is an integer from one to a maximum of four;

$x_1$ and $x_3$ are integers from zero to four, and $x_2$ is an integer from zero to three;

$y_1$ is an integer from zero to about six and $y_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as:

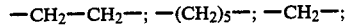

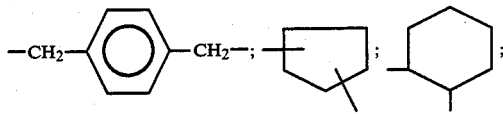

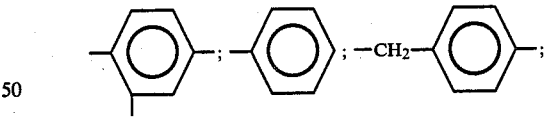

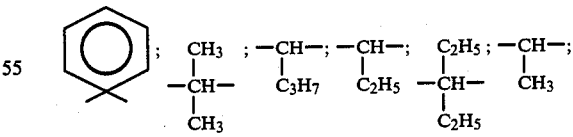

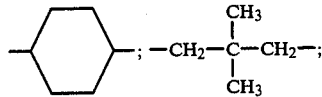

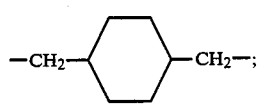

-continued

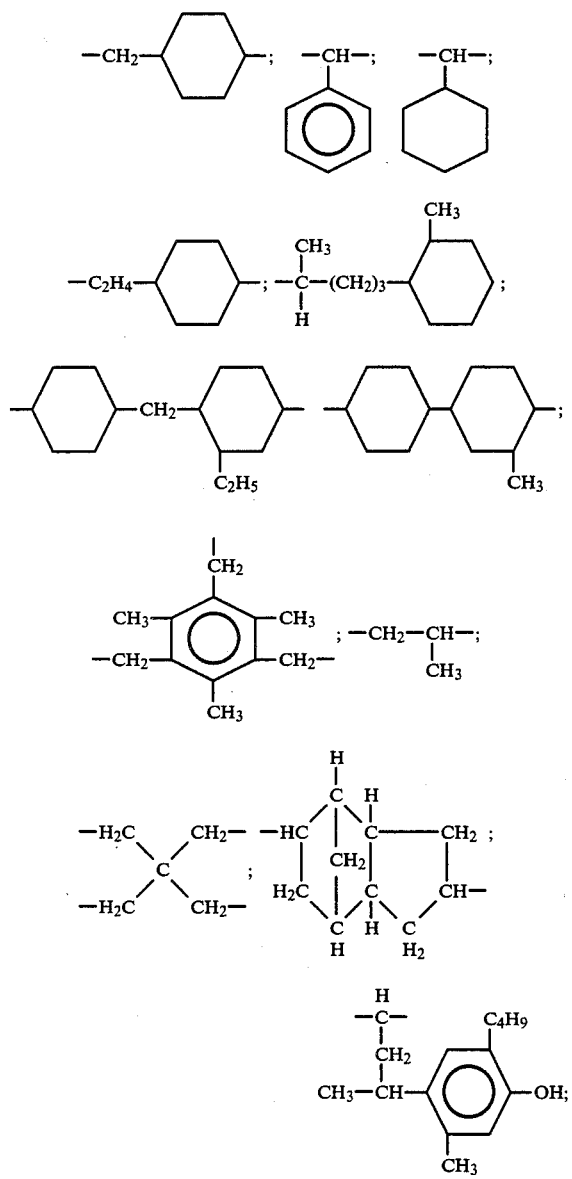

(2) Y groups where only atoms other than carbon link the aromatic rings, such as —O—, —S—, —S—, —S— and —(S)$_x$—
         ‖    ‖
         O    O

O where x is a number from one to ten;

(3) Y groups made up of more than a single atom including both carbon and other atoms linking the aromatic nuclei, such as:

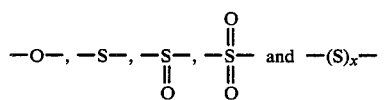

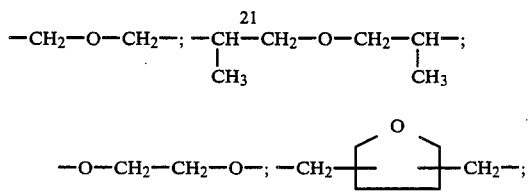

-continued

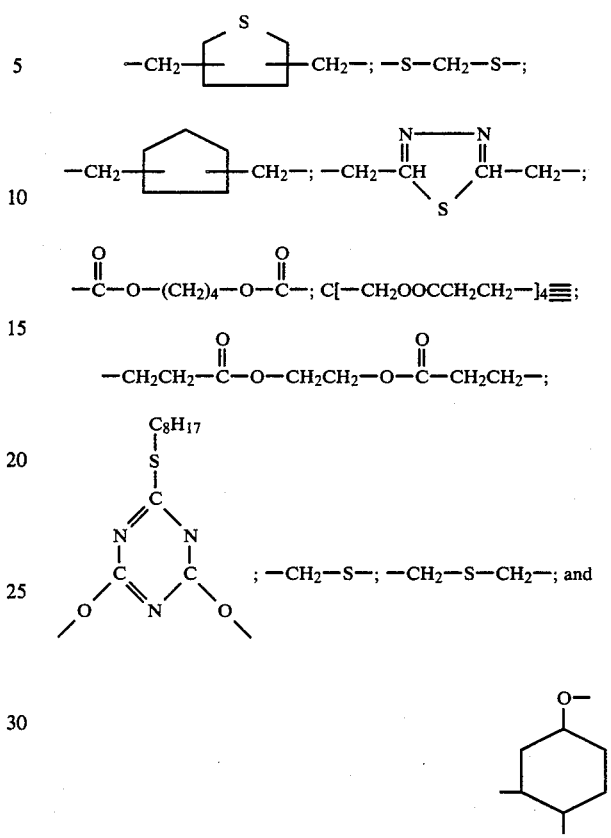

Although the relation of effectiveness to chemical structure is insufficiently understood, many of the most effective phenols have Y groups of subgenus (1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenyl-phenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxy-phenol, p-n-decyloxy-cresol, nonyl-n-decyloxycresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-dichlorobenzoyl-aminophenol, p-hydroxysalicyl anilide, stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl(4-hydroxy-3-methyl-5-t-butyl)benzylmalonate.

Exemplary polyhydric phenols are orcinol, propyl gallate, catechol, resorcinol, 4-octyl-resorcinol, 4-dodecylresorcinol, 4-octadecyl-catechol, 4-isooctyl-phloroglucinol, pyrogallol, hexahydroxybenzene, 4-isohexylcatechol, 2,6-di-tertiary-butyl-resorcinol, 2,6-di-isopropyl-phloroglucinol.

Exemplary polyhydric polycyclic phenols are methylene bis-(2,6-di-tertiary-butyl-phenol), 2,2-bis-(4-hydroxy phenyl)propane, methylene-bis-(p-cresol), 4,4'-benzylidene bis(2-tertiary-butyl-5-methyl-phenol), 4,4'-cyclo-hexylidene bis-(2-tertiary-butylphenol), 2,2'-methylene-bis-(4-methyl-6-(1'-methyl-cyclohexyl)-phenol), 2,6-bis-(2'-hydroxy-3'-tertiary-butyl-5'-methyl-benzyl)-4-methylphenol, 4,4'-bis-(2-tertiary-butyl-5-methyl-phenol), 2,2'-bis-(4-hydroxy-phenyl)butane, ethylene bis-(p-cresol), 4,4'-oxobis-phenol, 4,4'-oxobis-(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol; 4,4'-thio-bis-(3-methyl-6-tertiary-butyl-phenol), 2,2'-thio-bis-(4-methyl-6-tertiary-butyl-phenol), 4,4'-n-butylidene-(2-t-butyl-5-methylphenol), 2,2'-methylene-bis-(4-methyl-6-(1'-methyl-cyclohexyl)phenol), 4,4'-cyclohexylene bis-(2-tertiary-butyl-phenol), 2,6-bis-(2'-hydroxy-3'-t-butyl-5'-methyl-benzyl)-4-methyl-phenol, tert-butylphenyl)butane, 1,8-bis-(2-hydroxy-5-methyl-benzoyl-n-octane, 2,2'-ethylene-bis-[4'-(3-tert-butyl-4-hydroxyphenyl)-thiazole], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butylphenyl)butyric acid]glycol ester, 4,4'-butylidene-bis-(6-t-butyl-m-cresol), 1,1,3-tris-(2-methyl-4-hydroxy-5-t-butylphenyl)butane, 1,3,5-tris-(3,5-di-t-butyl-4-hydroxybenzyl)-2,4,6-trimethylbenzene, tetrakis[methylene-3 (3,5-di-t-butyl-4-hydroxyphenyl)propionate]methane, 1,3,5-tris-(3,5-di-t-butyl-4-hydroxybenzyl)isocyanurate, 1,3,5-tris-(3,5-di-t-butyl-4-hydroxyphenyl)propionyl-oxyethyl isocyanurate, 2-octylthio-4,6-di-(4-hydroxy-3,5-di-t-butyl)phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicyclopentadiene polyphenols, which are of the type:

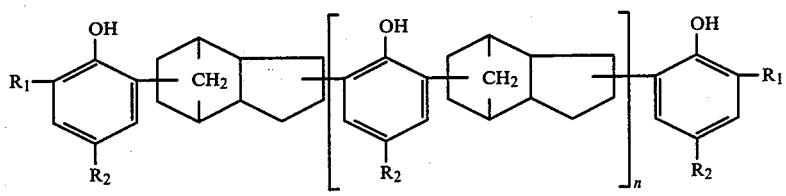

4,4'-oxobis(naphthalene-1,5-diol), 1,3'-bis-(naphthalene-2,5-diol)propane, and 2,2'-butylene bis-(naphthalene-2,7-diol), (3-methyl-5-tert-butyl-4-hydroxyphenyl)-4'-hydroxy-phenyl)propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl)ethane, (2-hydroxy-phenyl)-(3',5'-di-tert-butyl-4',4-hydroxyphenyl)ethane, 2,2'-methylene-bis-(4-octylphenol), 4,4'-propylene-bis-(2-tert-butylphenol), 2,2'-isobutylene-bis-(4-nonylphenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis-(3-t-butyl-4-hydroxyphenyl)thiazolo-(5,4-d)thiazole, 2,2'-bis-(3-methyl-5-t-butyl-4-hydroxyphenyl)thiazolo-(5,4-d)-thiazole, 4,4'-bis-(4-hydroxyphenyl)pentanoic acid octadecyl ester, cyclopentylene-4,4'-bis-phenol, 2-ethylbutylene-4,4'-bisphenol, 4,4'-cyclooctylene-bis-(2-cyclohexylphenol), β,β-thiodiethanol-bis-(3-tert-butyl-4-hydroxyphenoxy acetate), 1,4-butanedio-bis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl)sulfide, bis-(2-tert-butyl-4-hydroxy-5-methylphenyl)sulfide, bis-(2-tert-butyl-4-hydroxy-5-methylphenyl)sulfoxide, bis-(3-ethyl-5-tert-butyl-4-hydroxybenzyl)sulfide, bis-(2-hydroxy-4-methyl-6-tert-butyl-phenyl)sulfide, 4,4'-bis-(4-hydroxyphenyl)pentanoic acid octadecyl thiopropionate ester, 1,1,3-tris-(2'-methyl-4-hydroxy-5'-tert-butylphenyl)butane, 1,1,3-tris-(1-methyl-3-hydroxy-4- in which
R$_1$ and R$_2$ are lower alkyl, and can be the same or different, and
n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

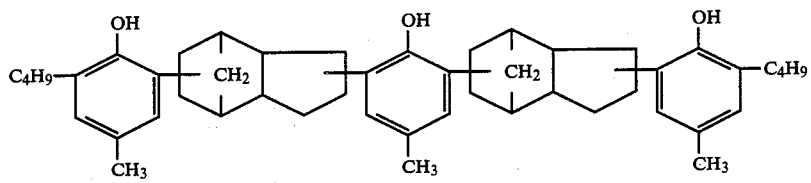

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. No. 3,124,555, U.S. Pat. No. 3,242,135, and British patent No. 961,504.

When the stabilizer composition is used in conjunction with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicyclic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts can be used but water-soluble salts are preferred for use with aqueous solutions and dispersions of the piperidyl quaternary ammonium halides. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophisphites.

The organic triphosphites in which the radicals are monovalent radicals can be defined by the formula:

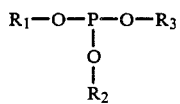

in which $R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

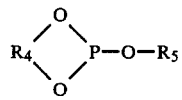

in which $R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$;

$R_5$ is hydrogen or a cation, in the case of the acid phosphites.

Also useful organic triphosphites are mixed heterocyclic-open chain phosphites of the type:

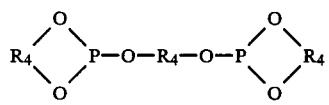

More complex triphosphites are formed from trivalent organic radicals, of the type:

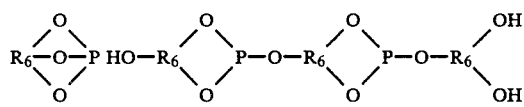

in which $R_6$ is a trivalent organic radical of any of the types of $R_1$ to $R_5$, inclusive, as defined above.

A particularly useful class of complex triphosphites are the tetraoxadiphosphaspiro undecanes of the formula:

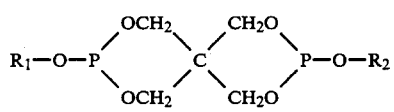

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula:

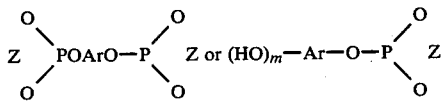

in which Ar is a mono or bicyclic aromatic nucleus and m is an integer of from 0 to about 5. Z is one or a plurality of organic radicals as defined above for $R_1$ to $R_6$, taken singly or together in sufficient number to satisfy the valences of the two phosphite oxygen atoms.

One or both Z radicals is also hydrogen, in the case of the acid phosphites, and can include additional bicyclic aromatic groups of the type $(HO)_m$—Ar.

The cation in the case of acid phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl)phosphite, trioctadecyl phosphite, triisooctyl phosphite, tridodecyl phosphite, isooctyl diphenyl phosphite, diisooctyl phenyl phosphite, tri(t-octylphenyl)phosphite, tri-(t-nonylphenyl)phosphite, benzyl methyl isopropyl phosphite, butyl dicresyl phosphite, isooctyl di(octylphenyl)phosphite, di(2-ethylhexyl)(isooctylphenyl)phosphite, tri(2-cyclohexylphenyl)phosphite), tri-α-naphthyl phosphite, tri(-phenylphenyl)phosphite, tri(2-phenylethyl)phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane (diphenyl-pentaerythritol diphosphite), 3,9-di(decyloxy)-2,4,8,10-tetraoxa-3,9-diphosphaspiro(5,5)-undecane, 3,9-di(isodecyloxy)-2,4,8,10-tetaroxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(-lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(butoxyethoxyethyloxy)-2,4,8,10-tetraoxa-3,9-diphosphaspiro-(5,5)-undecane, 3,9-di(methoxyethoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane where the (polyethoxy)ethyloxy group has an average molecular weight of 350), 3,9-di(methoxy(polyethoxy)ethyloxy)-2,4,8,10-tetraoxa-3,9-diphosphaspiro-(5,5)-undecane (where the (polyethoxy)ethyloxy group has an average molecular weight of 550).

Exemplary of the bis aryl triphosphites are: bis(4,4'-thio-bis(2-tertiary-butyl-5-methyl-phenol))isooctyl phosphite, mono(4,4'-thio-bis(2-tertiary-butyl-5-methylphenol))di-phenyl phosphite, tri-(4,4'-n-butylidenebis(2-tertiary-butyl-5-methylphenol))phosphite, (4,4'-benzylidene-bis(2-tertiary-butyl-5-methyl-phenol)-)diphenyl phosphite, isooctyl 2,2'-bis(-parahydroxyphenyl)propane phosphite, decyl 4,4'-n-butylidene-bis(2-tertiary-butyl-5-methylphenol)phosphite, tri-4,4'-thio-bis(2-tertiary-butyl-5-methylphenol)phosphite, 2-ethylhexyl-2,2'-methylene-bis(4-methyl-6,1'-methylcyclohexyl)phenol phosphite, tri(2,2'-bis-(para-hydroxyphenyl)propane)phosphite, tri(4,4'-thio-bis(2-tertiary-butyl-5-methyl-phenol)phosphite, isooctyl(2,6-bis(2'-hydroxy-3,5-dinonylbenzyl)-4-nonyl phenyl))phosphite, tetra-tridecyl-4,4'-n-butylidene-bis(2-tertiary-butyl-5-methylphenyl)diphosphite, tetra-isooctyl-4,4'-thio-bis(2-tertiary-butyl-5-methylphenyl)diphosphite, 2,2'-methylene-bis(4-methyl-6,1'-methyl cyclohexyl phenyl)polyphosphite, isooctyl-4,4'-isopropylidene-bisphenyl polyphosphite, 2-ethylhexyl-2,2'-methylene-bis(4-methyl-6,1'-methyl-cyclohexyl)phenyl triphosphite, tetra-tridecyl-4,4'-oxydiphenyl diphosphite, tetra-n-dodecyl-4,4'-n-butylidene bis(2-tertiary-butyl-5-methylphenyl)diphosphite, tetra-tridecyl-4,4'-isopropylidene disphenyl diphosphite, hexa-tridecyl butane-1,1,3-tris(2'-methyl-5'-tertiary-butylphenyl-4')triphosphite.

Exemplary acid phosphites are di(phenyl)phosphite, monophenyl phosphite, mono(diphenyl)phosphite, dicresyl phosphite, di-(o-isooctylphenyl)phosphite, di(p-ethylhexylphenyl)phosphite, di(p-t-octylphenyl)phosphite, di(dimethylphenyl)phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl)phosphite, monocyclohexyl phosphite, dicyclohexyl phosphite, di(2-cyclohexyl phenyl)phosphite, di-α-naphthyl phosphite, diphenyl phenyl phosphite, di(diphenyl)phosphite, di-(2-phenyl ethyl)phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenol))-phosphite, (4,4'-thio-bis(2-tertiary-butyl-5-methylphenol))phenyl phosphite, bis(4,4'-n-butylidene-bis(2-tertiary-butyl-5-methylphenol))phosphite, mono(4,4'-benzylidene-bis(2-tertiary-butyl-5-methylphenol))-phosphite, mono(2,2'-bis-(parahydroxyphenyl)-propane)phosphite, mono(4,4'-butylidene-bis(2-tertiary-butyl-5-methylphenol)phosphite, bis(4,4'-thio-bis(2-tertiary-butyl-5-methylphenol))phosphite, mono-2-ethylhexyl-mono-2,2'-methylene-bis(4-methyl-6,1'-methyl-cyclohexyl)phenol phosphite, bis(2,2'-bis(para-hydroxyphenyl)propane)phosphite, monoisooctyl-mono(4,4'-thio-bis(2-tertiary-butyl-5-methylphenol))phosphite, isooctyl-(2,6-bis(2'-hydroxy-3,5-dinonylbenzyl)-4-nonylphenyl))phosphite, tri-tridecyl-4,4'-n-butylidene-bis(2-tertiary-butyl-5-methylphenyl)diphosphite, triisooctyl-4,4'-thio-bis(2-tertiary-butyl-5-methylphenyl)-diphosphite, bis(2,2'-methylene-bis(4-methyl-6,1'-methyl cyclohexyl phenyl))phosphite, isooctyl-4,4'-isopropylidene-bis-phenyl phosphite, monophenyl mono(2,2'-methylene-bis(4-methyl-6,1'-methyl-cyclohexyl))triphosphite, di-tridecyl-4,4'-oxydiphenyl diphosphite, di-n-dodecyl-4,4'-n-butylidene-bis(2-tertiary-butyl-5-methylphenyl)diphosphite, di-tridecyl-4,4'-isopropylidene bisphenyl diphosphite, tetra-tridecyl butane-1,1,3-tris(2'-methyl-5-tertiary-butylphenyl-4)-triphosphite.

The thiodipropionic acid ester has the following formula:

$$R_1OOCCH_2CH_2-S-CH_2CH_2COOY$$

in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals: and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

$$-XO[OCCH_2CH_2SCH_2CH_2COOXO]_nOCCH_2CH_2-S-CH_2CH_2COOZ$$

where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylene-arylene and mixed alkylenecycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming within the above-designated categories within the general formula can be defined as follows:
(a) $R_1OOCCH_2CH_2SCH_2CH_2COOH$
(b) $R_1OOCCH_2CH_2SCH_2CH_2COOR_2$
(c) $R_1O[OCCH_2CH_2SCH_2CH_2COOX-O]_nOCCH_2CH_2SCH_2CH_2COOZ$
(d) $R_1OOCCH_2CH_2SCH_2CH_2COOM$ In the above formulae $R_1$ and $R_2$, M, X and Z are the same as before and the value of $n_1$ can range upwards from 1, but there is no upper limit on $n_1$ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, $R_2$ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as 1,2-propylene,

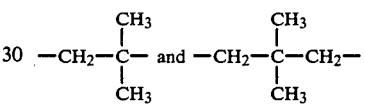

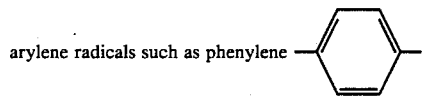
arylene radicals such as phenylene

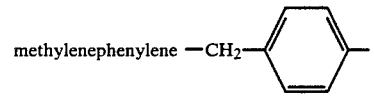
methylenephenylene —CH$_2$—

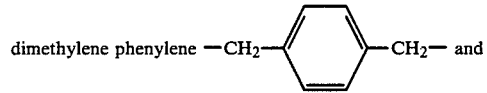
dimethylene phenylene —CH$_2$— —CH$_2$— and

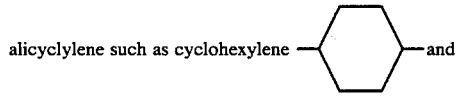
alicyclylene such as cyclohexylene —— and

cyclopentylene

As exemplary of the thiodipropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl)thiodipropionic acid.

These esters are for the most part known compounds, but where they are not available, they are readily prepared by esterification of thiodipropionic acid and the corresponding alcohol.

Also useful are:

(1) Thioalkanoic acid amides of Tokuno et al Japanese patent No. 16,286/68 having the formula:

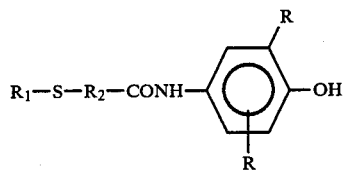

R is alkyl of one to eight carbon atoms, $R_1$ is alkyl of six to twenty-four carbon atoms, and $R_2$ is alkylene of one to six carbon atoms.

(2) Thioalkanoic acid amides of 1,3,5-triazines of Ozeki et al Japanese patent No. 20,366/68 having the formula:

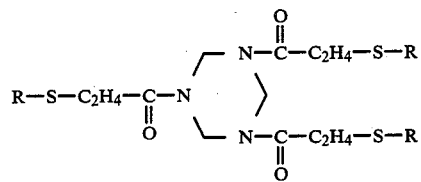

R is alkyl of eight to eighteen carbon atoms.

(3) Bis-thioalkanoic acid amides of Yamamoto et al Japanese patent No. 23,765/68 having the formula:

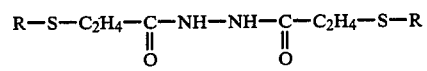

R is alkyl of more than six carbon atoms, aryl or aralkyl.

(4) Bis-thioalkylanoic acid amides of Ozeki et al Japanese patent No. 26,184/69 having the formula:

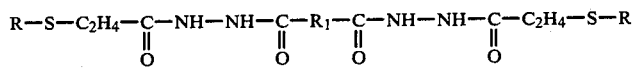

R is alkyl of twelve to eighteen carbon atoms, and $R_1$ is alkylene of one to ten carbon atoms, cycloalkylene, or arylene.

(5) Bis-alkylene thioalkanoic acid amides of Ozeki Japanese patent No. 31,464/69 having the formula:

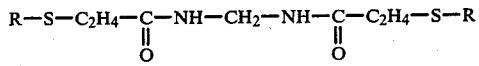

R is alkyl of more than six carbon atoms, aryl, or aralkyl.

(6) Thioalkanoic acid amide derivatives of Minagawa et al, published Japanese application No. 106,484/74 having the formula:

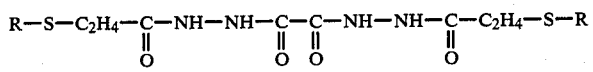

R is hydrocarbyl of one to twenty carbon atoms.

(b 7) Alkylene bis-thioalkanoic acid amides of U.S. Pat. No. 4,279,805 to Ohzeki et al, patented July 21, 1981, having the general formula:

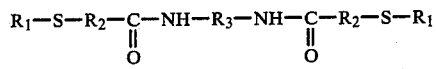

wherein:
$R_1$ is alkyl having from one to about fifty carbon atoms;
$R_2$ is alkylene having from one to about three carbon atoms; and
$R_3$ is alkylene having from about two to about twelve carbon atoms.

β-Alkylthiopropionic acid esters having the general formula:

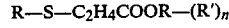

wherein:
R is alkyl of four to twenty carbon atoms;
n is a number from 1 to 6; and
R' is the residue of an alcohol having from one to six hydroxyl groups.

Pentaerythritol tetra dodecyl thio propionate is an example of this group.

Other conventional light stabilizers can be employed, such as hydroxybenzophenones such as 2-hydroxy-4-methoxybenzophenone, 2-hydroxy-4-n-octoxy benzophenone, 2,4-dihydroxybenzophenone, benzotriazoles, such as 2(2-hydroxy-5-methylphenyl)benzotriazoles, 2(2-hydroxy-3-t-butyl-5-methylphenyl)-5-chlorobenzotriazole, 2(2-hydroxy-3-5-di-t-butylphenyl)5-chlorobenzotriazole, 2(2-hydroxy-3,5-di-t-amylphenyl)benzotriazole, benzoates such as phenylsalicylate, 2,4-di-t-butylphenyl-3,5-di-t-butyl-4-hydroxy phenylbenzoate, nickel compounds such as nickel-2,2'-thiobis(4-t-octylphenolate), nickel-monoethyl(3,5-di-t-butyl-4-hydroxybenzyl)phosphonate, substituted acrylonitriles such as methyl-α-cyano-β-methyl-β-(p-methoxyphenyl)acrylate and oxalic anilides such as N-2-ethyl phenyl-N'-2-ethoxy-5-t-butyl phenyl oxalic diamide, N-2-ethyl phenyl-N'-2-ethoxy phenyl oxalic diamide.

A sufficient amount of the stabilizer or combination is used to improve the resistance of the synthetic polymer to deterioration in physical properties when exposed to heat and light, including, for example, discoloration, reduction in melt viscosity and embrittlement. Very small amounts are usually adequate. Amounts within the range from about 0.001 to about 5% total stabilizers including the piperidyl quaternary ammonium halide of the invention by weight of the polymer are satisfactory. Preferably, from 0.01 to 3% is employed for optimum stabilization.

The stabilizer systems of the invention are readily rendered in solid particulate form, comprising a blend of:

(a) piperidyl quaternary ammonium halide light stabilizer in an amount of from about 10 to about 35 parts by weight;

and optionally:

(b) a phenolic antioxidant in an amount from about 10 to about 35 parts by weight; and/or (c) other heat or light stabilizers in an amount of from about 10 to about 35 parts by weight.

The piperidyl quaternary ammonium halide light stabilizer of the invention can be employed in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds; and organic phosphites.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadiene-styrene terpolymers, other antioxidants and polyvalent metal salts of the higher fatty acids can be used.

In addition, other conventional additives for synthetic polymers, such as plasticizers, lubricants, emulsifiers, antistatic agents, flame-proofing agents, pigments and fillers, can be employed.

The stabilizer or combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement on ageing and heating.

The following Examples in the opinion of the inventors represent preferred embodiments of synthetic resin compositions containing piperidyl quaternary ammonium compounds of the invention.

EXAMPLES 1 TO 4

A series of polypropylene compositions was prepared using quaternary ammonium compounds of the invention and having the following formulation:

| Ingredient | Parts by Weight |
| --- | --- |
| Polypropylene | 100 |
| Stearyl-β-3,5-di-tert-butyl-4 hydroxyphenyl propionate | 0.2 |
| Stabilizer as shown in Table I | 0.3 |

The compositions were thoroughly blended in a Brabender Plastograph, and then compression-molded to form sheets 0.3 mm thick. Pieces 2.5 cm$^2$ were cut off from the sheets, and exposed to a high voltage mercury lamp.

The following stabilizers were employed:

TABLE I

| Example No. | Stabilizer |
| --- | --- |
| Example 1 | N,N—Dimethyl-N—butyl-N—(1,2,2,6,6-pentamethyl-4-piperidyl)ammonium bromide |
| Example 2 | N,N—Dimethyl-N—butyl-N—(1,2,2,6,6-pentamethyl 4 piperidyl)ammonium iodide |
| Example 3 | N,N—Dimethyl N—octyl-N(1,2,2,6,6-pentamethyl-4-piperidyl)ammonium iodide |
| Example 4 | N,N,N',N'—Tetramethyl N,N' bis(1,2,2,6,6-pentamethyl 4-piperidyl)hexamethylene diammonium diiodide |

The compounds of the invention considerably enhance the resistance of the polypropylene composition to deterioration upon exposure to ultraviolet light.

EXAMPLES 5 TO 8

Ethylene-vinyl acetate copolymer compositions were prepared using piperidyl quaternary ammonium compounds of the invention and having the following formulation:

| Ingredient | Parts by Weight |
| --- | --- |
| Ethylene-vinyl acetate copolymer | 100 |
| 2,6-Di-t butyl-p cresol | 0.1 |
| Ca stearate | 0.1 |
| Zn stearate | 0.1 |
| Diisodecyl phenyl phosphite | 0.2 |
| Stabilizer as shown in Table II | 0.2 |

The stabilizer was blended with the polymer on a two-roll mill at 130° C., and sheets 0.4 mm thick were then compression molded at 140° C. from the resulting blend Pieces 2.5 cm square were cut off from the sheets, and exposed to ultraviolet light in a Weather-O Meter for 500 hours. At the start and at the conclusion of the test, tensile strength of the sheet samples was determined.

The following quaternary ammonium compounds were tested:

TABLE II

| Example No. | Stabilizer |
|---|---|
| Example 5 | N,N Dimethyl N butyl-N—(1,2,2,6,6 pentamethyl-4-piperidyl)ammonium bromide |
| Example 6 | N,N—Dimethyl-N butyl N—(1,2,2,6,6 pentamethyl-4-piperidyl)ammonium iodide |
| Example 7 | N,N—Dimethyl N—octyl N—(1,2,2,6,6-pentamethyl-4-piperidyl)ammonium iodide |
| Example 8 | N,N,N',N' Tetramethyl-N,N'—bis(1,2,2,6,6-pentamethyl-4 piperidyl)hexamethylene diammonium diiodide |

The compounds of the invention considerably enhance the resistance of the ethylene vinyl acetate copolymer composition to deterioration upon exposure to ultraviolet light.

EXAMPLES 9 TO 12

Polyvinyl chloride resin compositions were prepared using piperidyl quaternary ammonium compounds of the invention and having the following formulation:

| Ingredient | Parts by Weight |
|---|---|
| Polyvinyl chloride | 100 |
| Dioctyl phthalate | 48 |
| Epoxidized soybean oil | 2 |
| Tris(nonylphenyl)phosphite | 0.2 |
| Ca stearate | 1.0 |
| Zn stearate | 0.1 |
| Stabilizer as shown in Table III | 0.3 |

This formulation was blended and sheeted off on a two-roll mill to form sheets 1 mm thick. The light resistance of these sheets was then determined by placing strips 1 cm wide in a Weather-O-Meter, and exposing them to ultraviolet light. The time in hours was then noted for the sheets to develop a noticeable discoloration and/or embrittlement, indicating deterioration due to oxidation in the presence of ultraviolet light.

The piperidyl quaternary ammonium compounds tested are shown in Table III.

TABLE III

| Example No. | Stabilizer |
|---|---|
| Example 9 | N,N—Dimethyl-N—butyl-N—(1,2,2,6,6-pentamethyl-4-piperidyl)ammonium bromide |
| Example 10 | N,N—Dimethyl-N—butyl-N—(1,2,2,6,6-pentamethyl-4-piperidyl)ammonium iodide |
| Example 11 | N,N—Dimethyl-N octyl N—(1,2,2,6,6-pentamethyl-4-piperidyl)ammonium iodide |
| Example 12 | N,N,N',N'—Tetramethyl-N,N'—bis(1,2,2,6,6-pentamethyl-4-piperidyl)hexamethylene diammonium diiodide |

The compounds of the invention considerably enhance the resistance of the polypropylene composition to deterioration upon exposure to ultraviolet light.

EXAMPLES 13 TO 16

Polypropylene compositions were prepared having the following formulation:

| Ingredient | Parts by Weight |
|---|---|
| Polypropylene | 100 |
| Stearyl-β-(3,5-di-t-butyl-4-hydroxy-phenyl)propionate | 0.15 |
| Calcium stearate | 0.05 |
| Sample compound as shown in Table IV | 0.3 |

The compositions were thoroughly blended in a Brabender Plast-O-Graph, and then compression-molded to prepare sheets 0.3 mm thick. Pieces 2.5 cm² were cut off from the sheets, and exposed to a high pressure mercury lamp. The time in hours when degradation set in, as determined by a significant discoloration and/or embrittlement, was noted as hours to failure, and the results are set forth in Table IV.

The surface resistivity and charged voltage of the test specimens were determined at 25° C. and at 50% humidity to test the antistatic effects of the compounds. The results are shown in Table IV.

TABLE IV

| Example No. | Sample compound | Hours to Failure | Surface Resistivity Ω | Charged Voltage |
|---|---|---|---|---|
| | None | 100 | $4.41 \times 10^{17}$ | 1080 |
| Control 1 | Lauryltrimethylammonium chloride | 100 | $2.85 \times 10^{15}$ | 790 |
| Control 2 | N—Methyl-N—butyl-N—(1,2,2,6,6-pentamethyl-4-piperidyl) amine | 540 | $4.10 \times 10^{17}$ | 1040 |
| Example 13 | N,N—Dimethyl-N—butyl-N—(1,2,2,6,6-pentamethyl-4-piperidyl) ammonium bromide | 540 | $1.20 \times 10^{15}$ | 710 |
| Example 14 | N,N—Dimethyl-N—butyl-N—(1,2,2,6,6-pentamethyl-4-piperidyl) ammonium iodide | 520 | $1.45 \times 10^{15}$ | 730 |
| Example 15 | N,N—Dimethyl-N—octyl-N—(1,2,2,6,6-pentamethyl-4-piperidyl) ammonium iodide | 510 | $1.62 \times 10^{15}$ | 730 |
| Example 16 | N,N,N'N'—Tetramethyl-N,N'—bis(1,2,2,6,6-pentamethyl-4-piperidyl) hexamethylene-diamine diiodide | 560 | $1.38 \times 10^{15}$ | 720 |

The compounds of the invention considerably enhance the resistance of the polypropylene composition to deterioration upon exposure to ultraviolet light.

EXAMPLES 17 TO 20

Water soluble ink compositions were prepared by mixing the following formulation in a beaker.

| Ingredient | Parts by Weight |
|---|---|
| Direct Black (C.I. 35255) | 10.0 |
| Ethyleneglycol | 10.0 |
| Diethyleneglycol | 10.0 |
| Propyleneglycol | 10.0 |
| Polyoxyethylene ether | 0.2 |
| Water | 65.0 |

-continued

| Ingredient | Parts by Weight |
|---|---|
| Sample compound as shown in Table V | 0.3 |

Lines 10 mm width were drawn on the paper using the water soluble ink, and exposed to a fluorescent lamp (120 W) for 10 hours. The gloss index before and after irradiation was noted and the results are shown in Table V as gloss index retained.

TABLE V

| Example No. | Sample compound | Gloss Index Retained % |
|---|---|---|
| | None | 41 |
| Control 1 | N—Methyl-N—butyl-N—(1,2,2,6,6-pentamethyl-4-piperidyl)amine | 57 |
| Example 17 | N,N—Dimethyl-N—butyl-N—(1,2,2,6,6-pentamethyl-4-piperidyl) ammonium bromide | 85 |
| Example 18 | N,N—Dimethyl-N—butyl-N—(1,2,2,6,6-pentamethyl-4-piperidyl) ammonium iodide | 83 |
| Example 19 | N,N—Dimethyl-N—octyl-N—(1,2,2,6,6-pentamethyl-4-piperidyl) ammonium iodide | 82 |
| Example 20 | N,N,N',N'—Tetramethyl-N,N'—bis(1,2,2,6,6-pentamethyl-4-piperidyl)hexamethylenediamine diiodide | 85 |

The superiority of the quaternary ammonium compounds of the invention is evident from the data.

EXAMPLES 21 TO 24

A red pigment (2-(2,4-di-t-amylphenoxy)butyric acid 2-hydroxy-3,5-dichloro-4-methylanilide) 0.25 g and 0.25 g of the sample compound as shown in Table VI were dissolved in 10 ml of tricresylphosphate/ethylacetate mixed solvent.

Gelatin solution (6%) 70 ml and 10 ml of 4% aqueous solution of polyoxyethylenenonylphenylether were added and stirred to prepare an emulsion.

Silver bromide emulsion contains 0.6% silver 20 ml and 45 ml of water were added into 25 ml of the above emulsion and stirred. The resulting mixture was coated onto white paper and dried for three days.

The test pieces were cut off from the paper and exposed to 3000 lux.sec. of light and then treated with Kodak Ektaprint 2. The test pieces were aged for 28 days at 60° C. and 70% relative humidity.

The density of color of the pieces before and after aging was determined by densitometer and the results are shown in Table VI as % density retained.

TABLE VI

| Example No. | Sample compound | % Density Retained |
|---|---|---|
| | None | 54% |
| Control 1 | N—Methyl-N—butyl-N—(1,2,2,6,6-pentamethyl-4-piperidyl)amine | 62 |
| Example 21 | N,N—Dimethyl-N—butyl-N—(1,2,2,6-pentamethyl-4-piperidyl) ammonium bromide | 75 |
| Example 22 | N,N—Dimethyl-N—butyl-N—(1,2,2,6,6-pentamethyl-4-piperidyl) ammonium iodide | 73 |
| Example 23 | N,N—Dimethyl-N—octyl-N—(1,2,2,6,6-pentamethyl-4-piperidyl) ammonium iodide | 73 |
| Example 24 | N,N,N',N'—Tetramethyl-N,N'—bis(1,2,2,6,6-pentamethyl-4-piperidyl)hexamethylenediamine diiodide | 76 |

The superiority of the quaternary ammonium compounds of the invention is evident from the data.

EXAMPLES 25 TO 28

The compounds of this invention are effective light stabilizers for cationic electro-deposition coating.

Preparation of electro-deposition coating

Toluenediisocyanate 174 g and 2-ethylhexanol 130 g were stirred at below 100° C. Then, butadiene/acrylonitrile copolymer having terminal hydroxyls (M.W. 3500) 1800 g and dibutyltindilaurate 0.08 g were added and stirred for 90 minutes at 121° C. The product was diluted with 500 g of ethyleneglycol monoethylether. (Component A)

Bisphenol A-polyglycidylether (epoxy equivalent 910) 1000 g, N-methyl pyrrolidone 277 g and diethylamine 80.3 g were stirred for 2 hours at 100° C. to prepare amine-epoxy adduct. (Component B)

The mixture of 271 g of component A and 1357 g of component B was neutralized with 30 g of acetic acid and diluted with 50 g of water.

The above vehicle 100 g, titanium dioxide 8 g, basic lead silicate 2 g, carbon black 3 g, strontium chromate 2 g, dibutyltin dilaurate 1 g, water 209 g and sample compound 0.5 g were mixed to prepare electro-deposition coating.

Pieces of steel sheeting which were coated with primer were deposited with the above electro-deposition coating and then cured at 200° C. for 20 minutes.

The coated sheets were exposed to ultraviolet light in a Dew Panel Weather Meter for 3000 hours and the formation of cracks on the surface of the sheet were noted. The results are shown in Table VII.

TABLE VII

| Example No. | Sample compound | Formation of Cracks |
|---|---|---|
| | None | Extreme |
| Control 1 | N—Methyl-N—butyl-N—(1,2,2,6,6-pentamethyl-4-piperidyl)amine | Extreme |
| Example 25 | N,N—Dimethyl-N—butyl-N—(1,2,2,6,6-pentamethyl-4-piperidyl) ammonium bromide | None |
| Example 26 | N,N—Dimethyl-N—butyl-N—(1,2,2,6,6-pentamethyl-4-piperidyl) ammonium iodide | None |
| Example 27 | N,N—Dimethyl-N—octyl-N—(1,2,2,6,6-pentamethyl-4-piperidyl) ammonium iodide | None |
| Example 28 | N,N,N',N'—Tetramethyl-N,N'—bis(1,2,2,6,6-pentamethyl-4-piperidyl)hexamethylenediamine diiodide | None |

The superiority of the quaternary ammonium compounds of the invention is evident from the data.

Having regard to the foregoing disclosure, the following is claimed as inventive and patentable embodiments thereof:

1. 2,2,6,6-Tetramethyl piperidyl quaternary ammonium halides having the formula:

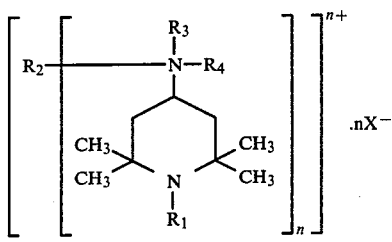 (I)

wherein:
  $R_1$, $R_3$ and $R_4$ are alkyl having from one to about twelve carbon atoms;
  n is 1 or 2;
  when n is 1, $R_2$ is alkyl having from one to about twelve carbon atoms; and
  when n is 2, $R_2$ is alkylene having from one to about twelve carbon atoms; and
  X is halogen as well as stabilizer compositions and synthetic resin compositions containing the same.

2. A compound according to claim 1, in which $R_2$ is alkyl and n is 1.

3. A compound according to claim 1, in which $R_2$ is alkylene and n is 2.

4. A compound according to claim 1, in which X is chloride.

5. A compound according to claim 1, in which $R_1$, $R_2$, $R_3$ and $R_4$ are alkyl, n is 1 and X is chloride.

6. A compound according to claim 1, in which $R_1$, $R_2$, $R_3$ and $R_4$ are alkyl, n is 1 and X is bromide.

7. A compound according to claim 1, in which $R_1$, $R_3$ and $R_4$ are alkyl, $R_2$ is alkylene, n is 2 and X is chloride.

8. A compound according to claim 1, in which $R_1$, $R_3$ and $R_4$ are alkyl, $R_2$ is alkylene, n is 2 and X is bromide.

9. A compound according to claim 1 having the structure:

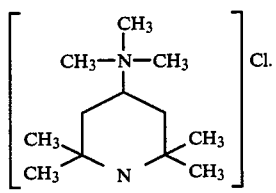

10. A compound according to claim 1 having the structure:

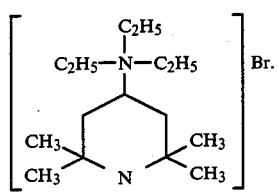

11. A compound according to claim 1 having the structure:

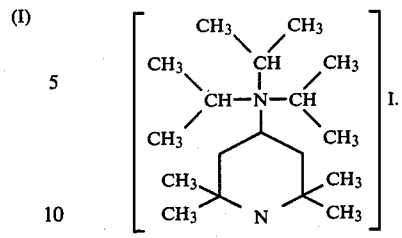

12. A compound according to claim 1 having the structure:

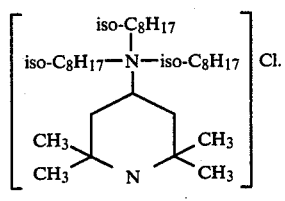

13. A compound according to claim 1 having the structure:

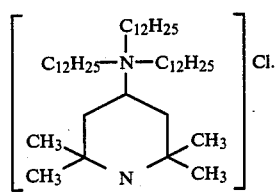

14. A compound according to claim 1 having the structure:

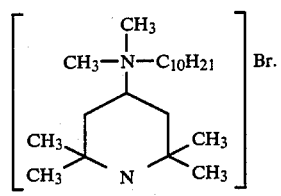

15. A polyvinyl chloride resin composition having improved resistance to deterioration upon exposure to light comprising a polyvinyl chloride resin formed at least in part of the recurring group:

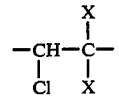

and having a chlorine content in excess of 40%, where X is either hydrogen or chlorine; and a compound in accordance with claim 1.

16. A polyvinyl chloride resin composition in accordance with claim 15 in which the polyvinyl chloride resin is polyvinyl chloride homopolymer.

17. A polyvinyl chloride resin composition in accordance with claim 15 in which the polyvinyl chloride resin is a copolymer of vinyl chloride and vinyl acetate.

18. An olefin polymer composition having improved resistance to deterioration upon exposure to light comprising an olefin polymer selected from the group consisting of polymers of alpha-olefins having from two to six carbon atoms and polystyrene, and a compound in accordance with claim 1.

19. An olefin polymer composition in accordance with claim 18 wherein the polyolefin is polypropylene.

20. An olefin polymer composition in accordance with claim 18 wherein the polyolefin is polyethylene.

21. An olefin polymer composition in accordance with claim 18 wherein the polyolefin is ethylene-propylene copolymer.

22. An ethylene-vinyl acetate copolymer composition having improved resistance to deterioration upon exposure to light comprising an ethylene-vinyl acetate copolymer and a compound in accordance with claim 1.

23. 2,2,6,6-Tetramethyl piperidyl quaternary ammonium halides having the formula:

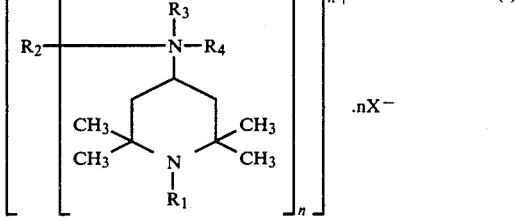

wherein:
$R_1$, $R_3$ and $R_4$ are selected from the group consisting of alkyl having from one to about twelve carbon atoms; alkyl having from eight to about twenty-two carbon atoms; and polyoxyalkylene having from six to about forty oxyalkylene units; the oxyalkylene having from two to about four carbon atoms and at least one of $R_1$, $R_3$ and $R_4$ is long chain aliphatic alkyl or polyoxyalkylene;
n is 1 or 2;
when n is 1, $R_2$ is alkyl having from one to about twelve carbon atoms; and
when n is 2, $R_2$ is alkylene having from one to about twelve carbon atoms; and
X is halogen
as well as stabilizer compositions and synthetic resin compositions containing the same.

* * * * *